(12) United States Patent
Baumgart

(10) Patent No.: US 8,778,029 B2
(45) Date of Patent: Jul. 15, 2014

(54) IMPLANTABLE PROSTHESIS FOR REPLACING A HUMAN HIP OR KNEE JOINT AND THE ADJOINING BONE SECTIONS

(76) Inventor: Rainer Baumgart, Munich (DE)

( * ) Notice: Subject to any disclaimer, the term of this patent is extended or adjusted under 35 U.S.C. 154(b) by 59 days.

(21) Appl. No.: 13/334,573

(22) Filed: Dec. 22, 2011

(65) Prior Publication Data
US 2012/0165950 A1    Jun. 28, 2012

(30) Foreign Application Priority Data
Dec. 23, 2010  (EP) .................................... 10196739

(51) Int. Cl.
 *A61F 2/32* (2006.01)
 *A61F 2/30* (2006.01)

(52) U.S. Cl.
 USPC ............. 623/22.4; 623/23.45; 623/20.36

(58) Field of Classification Search
 USPC ......... 623/23.49, 23.45, 23.15, 20.14, 20.36, 623/20.35, 22.11, 22.12, 22.4, 23.39; 606/62, 63, 67
 See application file for complete search history.

(56) References Cited

U.S. PATENT DOCUMENTS

| | | | | | |
|---|---|---|---|---|---|
| 2,998,007 | A | * | 8/1961 | Herzog | 606/63 |
| 3,024,785 | A | * | 3/1962 | Dobelle | 623/23.26 |
| 3,623,164 | A | * | 11/1971 | Bokros | 606/60 |
| 3,745,995 | A | * | 7/1973 | Kraus | 602/2 |
| 3,781,917 | A | * | 1/1974 | Mathys | 623/23.27 |
| 3,820,534 | A | * | 6/1974 | Kraus et al. | 602/2 |
| 3,977,398 | A | * | 8/1976 | Burstein | 606/62 |
| 4,195,367 | A | * | 4/1980 | Kraus | 623/23.49 |
| 4,204,531 | A | * | 5/1980 | Aginsky | 606/63 |
| 4,214,322 | A | * | 7/1980 | Kraus | 623/23.49 |
| 4,227,518 | A | * | 10/1980 | Aginsky | 606/63 |
| 4,292,695 | A | * | 10/1981 | Koeneman | 623/23.44 |
| 4,313,434 | A | * | 2/1982 | Segal | 606/62 |
| 4,337,773 | A | * | 7/1982 | Raftopoulos et al. | 606/62 |
| 4,355,427 | A | * | 10/1982 | Schneider | 623/19.14 |
| 4,589,883 | A | * | 5/1986 | Kenna | 623/23.35 |
| 4,608,052 | A | * | 8/1986 | Van Kampen et al. | 623/23.29 |
| 4,628,920 | A | * | 12/1986 | Mathys et al. | 606/62 |
| 4,775,381 | A | * | 10/1988 | Tari et al. | 623/23.18 |
| 4,784,124 | A | * | 11/1988 | Kaltenbrunner et al. | 606/63 |
| 4,791,919 | A | * | 12/1988 | Elloy et al. | 606/62 |
| 4,919,673 | A | * | 4/1990 | Willert et al. | 623/23.48 |
| 4,919,679 | A | * | 4/1990 | Averill et al. | 623/22.12 |
| 4,946,459 | A | * | 8/1990 | Bradshaw et al. | 606/62 |
| 4,978,323 | A | * | 12/1990 | Freedman | 600/12 |
| 5,030,236 | A | * | 7/1991 | Dean | 623/23.49 |
| 5,032,129 | A | * | 7/1991 | Kurze et al. | 623/23.49 |
| 5,057,103 | A | * | 10/1991 | Davis | 606/63 |
| 5,116,335 | A | * | 5/1992 | Hannon et al. | 606/62 |
| 5,163,958 | A | * | 11/1992 | Pinchuk | 623/23.49 |
| 5,167,666 | A | * | 12/1992 | Mattheck et al. | 623/23.27 |
| 5,263,955 | A | * | 11/1993 | Baumgart et al. | 606/63 |

(Continued)

FOREIGN PATENT DOCUMENTS

| | | |
|---|---|---|
| EP | 0432253 | 6/1991 |
| EP | 1371346 | 12/2003 |
| WO | 0240092 | 5/2002 |

*Primary Examiner* — Alvin J. Stewart
(74) *Attorney, Agent, or Firm* — Bachman & LaPointe, P.C.

(57) ABSTRACT

For replacing a human hip or knee joint and the adjoining bone sections, an implantable prosthesis is provided, comprising a joint replacement part (10), a shaft replacement part (12) and a rod-shaped shaft anchoring part (16) being insertable into an axial cavity (14) in the shaft replacement part (12).

14 Claims, 5 Drawing Sheets

(56) References Cited

U.S. PATENT DOCUMENTS

| | | | |
|---|---|---|---|
| 5,268,000 A * | 12/1993 | Ottieri et al. | 606/62 |
| 5,350,379 A * | 9/1994 | Spievack | 606/63 |
| 5,383,935 A * | 1/1995 | Shirkhanzadeh | 623/23.49 |
| 5,415,660 A * | 5/1995 | Campbell et al. | 606/62 |
| 5,429,638 A * | 7/1995 | Muschler et al. | 606/60 |
| 5,429,640 A * | 7/1995 | Shuler et al. | 606/64 |
| 5,443,466 A * | 8/1995 | Shah | 606/62 |
| 5,454,813 A * | 10/1995 | Lawes | 606/62 |
| 5,456,724 A * | 10/1995 | Yen et al. | 623/23.49 |
| 5,531,748 A * | 7/1996 | de la Caffiniere | 606/62 |
| 5,704,938 A * | 1/1998 | Staehlin et al. | 606/62 |
| 5,704,939 A * | 1/1998 | Justin | 606/63 |
| 5,766,180 A * | 6/1998 | Winquist | 606/104 |
| 6,019,761 A * | 2/2000 | Gustilo | 606/62 |
| 6,034,295 A * | 3/2000 | Rehberg et al. | 623/23.49 |
| 6,143,036 A * | 11/2000 | Comfort | 623/23.54 |
| 6,336,929 B1 * | 1/2002 | Justin | 606/62 |
| 6,387,096 B1 * | 5/2002 | Hyde, Jr. | 606/60 |
| 6,425,925 B1 * | 7/2002 | Grundei | 623/32 |
| 6,443,994 B1 * | 9/2002 | Kubein-Meesenburg et al. | 623/39 |
| 6,481,440 B2 * | 11/2002 | Gielen et al. | 128/898 |
| 6,482,238 B1 * | 11/2002 | Grundei | 623/32 |
| 6,485,522 B1 * | 11/2002 | Grundei | 623/38 |
| 6,503,249 B1 * | 1/2003 | Krause | 606/62 |
| 6,517,541 B1 * | 2/2003 | Sesic | 606/62 |
| 6,602,296 B1 * | 8/2003 | Day et al. | 623/23.49 |
| 6,627,321 B1 * | 9/2003 | Ellingsen et al. | 428/469 |
| 6,679,890 B2 * | 1/2004 | Margulies et al. | 606/94 |
| 6,709,466 B1 * | 3/2004 | Grundei | 623/32 |
| 6,770,100 B2 * | 8/2004 | Draenert | 623/23.26 |
| 6,824,566 B2 * | 11/2004 | Kana et al. | 623/20.15 |
| 6,827,343 B2 * | 12/2004 | Skiera | 267/154 |
| 6,843,808 B2 * | 1/2005 | Grundei | 623/32 |
| 6,918,910 B2 * | 7/2005 | Smith et al. | 606/60 |
| 7,029,431 B2 | 4/2006 | Apple et al. | |
| 7,125,423 B2 * | 10/2006 | Hazebrouck | 623/16.11 |
| 7,135,022 B2 * | 11/2006 | Kosashvili et al. | 606/63 |
| 7,485,149 B1 * | 2/2009 | White | 623/23.47 |
| 7,559,951 B2 * | 7/2009 | DiSilvestro et al. | 623/23.47 |
| 7,753,915 B1 * | 7/2010 | Eksler et al. | 606/105 |
| 7,909,883 B2 * | 3/2011 | Sidebotham | 623/23.55 |
| 7,998,218 B1 * | 8/2011 | Brown | 623/20.35 |
| 8,075,630 B2 * | 12/2011 | Ricci et al. | 623/23.74 |
| 8,197,551 B2 * | 6/2012 | Swain et al. | 623/23.49 |
| 8,226,731 B2 * | 7/2012 | Grundei | 623/32 |
| 8,252,063 B2 * | 8/2012 | Stauch | 623/23.47 |
| 8,419,801 B2 * | 4/2013 | DiSilvestro et al. | 623/23.47 |
| 8,512,416 B2 * | 8/2013 | Porter et al. | 623/32 |
| 2002/0111629 A1 * | 8/2002 | Phillips | 606/62 |
| 2002/0133156 A1 * | 9/2002 | Cole | 606/62 |
| 2003/0004513 A1 * | 1/2003 | Guzman et al. | 606/62 |
| 2003/0018393 A1 * | 1/2003 | Skiera | 623/35 |
| 2003/0032958 A1 * | 2/2003 | Soubeiran | 606/61 |
| 2003/0033019 A1 * | 2/2003 | Lob | 623/23.47 |
| 2003/0040806 A1 * | 2/2003 | MacDonald | 623/23.49 |
| 2003/0083746 A1 * | 5/2003 | Kuslich | 623/17.11 |
| 2003/0109878 A1 * | 6/2003 | Grundei | 606/53 |
| 2004/0030395 A1 * | 2/2004 | Blunn et al. | 623/18.12 |
| 2004/0122428 A1 * | 6/2004 | Johnstone | 606/62 |
| 2004/0254646 A1 | 12/2004 | Stone et al. | |
| 2005/0107790 A1 * | 5/2005 | Qian | 606/62 |
| 2005/0228503 A1 * | 10/2005 | Gundolf | 623/22.21 |
| 2005/0256586 A1 * | 11/2005 | Kraus et al. | 623/23.16 |
| 2006/0004459 A1 * | 1/2006 | Hazebrouck et al. | 623/18.12 |
| 2006/0089642 A1 * | 4/2006 | Diaz et al. | 606/60 |
| 2007/0073300 A1 * | 3/2007 | Attawia et al. | 606/73 |
| 2007/0250062 A1 * | 10/2007 | Ara Pinilla et al. | 606/62 |
| 2008/0200995 A1 * | 8/2008 | Sidebotham | 623/28 |
| 2009/0123509 A1 * | 5/2009 | Berkland et al. | 424/422 |
| 2010/0145337 A1 * | 6/2010 | Janna et al. | 606/67 |
| 2010/0168867 A1 * | 7/2010 | Swain et al. | 623/23.49 |
| 2010/0179551 A1 * | 7/2010 | Keller et al. | 606/67 |
| 2010/0241239 A1 | 9/2010 | Smith | |
| 2011/0060419 A1 * | 3/2011 | Choi et al. | 623/23.49 |
| 2012/0035734 A1 * | 2/2012 | Unwin et al. | 623/20.14 |
| 2012/0095463 A1 * | 4/2012 | Rains et al. | 606/63 |
| 2012/0209268 A1 * | 8/2012 | Overes | 606/62 |
| 2012/0209269 A1 * | 8/2012 | Pool et al. | 606/63 |
| 2012/0259264 A1 * | 10/2012 | Swain et al. | 604/9 |
| 2012/0259334 A1 * | 10/2012 | Splieth et al. | 606/63 |
| 2013/0006245 A1 * | 1/2013 | Stoneburner et al. | 606/63 |
| 2013/0012941 A1 * | 1/2013 | Dees et al. | 606/62 |
| 2013/0053847 A1 * | 2/2013 | Siravo et al. | 606/62 |
| 2013/0072932 A1 * | 3/2013 | Stauch | 606/63 |
| 2013/0123785 A1 * | 5/2013 | Fonte | 606/63 |
| 2013/0144291 A1 * | 6/2013 | Gonzalez-Hernandez | 606/62 |
| 2013/0166039 A1 * | 6/2013 | Shaw-Klein | 623/23.49 |

* cited by examiner

IMPLANTABLE PROSTHESIS FOR REPLACING A HUMAN HIP OR KNEE JOINT AND THE ADJOINING BONE SECTIONS

BACKGROUND OF THE INVENTION

The present invention relates to an implantable prosthesis for replacing a human hip or knee joint and the adjoining bone sections, wherein the prosthesis comprises a joint replacement part, a shaft replacement part being connectable to the joint replacement part or integral therewith and having a central cavity, as well as a rod-shaped shaft anchoring part being insertable into the cavity. An implantable prosthesis of this kind is known from EP 1 371 346 B1.

After resection of a bone tumor, the removed bone and the joint concerned can be replaced by a tumor prosthesis, and there is initially no difference in leg length. The prosthesis is anchored in the remaining bone, as described, for example, in EP 1 371 346 B1. When a difference in leg length develops due to growth, the bone can be osteotomized and the prosthesis can be provided with a distraction medullary nail instead of the shaft anchoring part for performing the callus distraction method. Distraction medullary nails of this kind are described, for example, in EP 0 432 253 B1.

If a second lengthening step is required, this procedure must be performed again. In any case, however, after completion of length growth, the distraction medullary nail, which cannot remain in place for permanent shaft anchoring, must be replaced by a stable shaft anchoring part. Exchange of a distraction medullary nail or replacement by a stable shaft anchoring part is often only possible if the joint components are decoupled, so that extensive operative exposure is required. Thus, in addition to resection of the tumor, at least two, in most cases even three extensive surgical operations are required near the joint in the region of the prothesis, which implies a considerable risk of infection.

Therefore the object underlying the invention is to considerably reduce the extent of a repeated surgical operation, and thus the risk of infection, in the case of a set tumor prosthesis while maintaining the advantages of bone lengthening according to the callus distraction method, wherein the artificial joint itself is to be touched as little as possible.

SUMMARY OF THE INVENTION

This object is achieved on the basis of the implantable prosthesis of above-mentioned type by the fact that the shaft anchoring part, at its side facing away from the joint replacement part, comprises locating means for forming a channel through the bone section at the side facing away from the joint replacement part from the outside, the channel being axially aligned with the shaft anchoring part and reaching up to the shaft anchoring part, and attachment means for engagement with a tool located outside the bone section through the channel for exerting at least a traction force on the shaft anchoring part, enabling to remove it from the bone section through the channel.

The locating means provided at the shaft anchoring part thus enables directed drilling or milling of a channel being axially aligned with the shaft anchoring part inserted in the bone section and having a diameter allowing passage of the shaft anchoring part. Thereafter the attachment means at the end side of the shaft anchoring part facing away from the joint replacement part enables engagement of a tool by means of which the shaft anchoring part can be withdrawn from the cavity of the shaft replacement part through the milled channel in the bone. Subsequently a distraction medullary mail can be introduced instead of the shaft anchoring part through the milled bone channel into the cavity of the shaft replacement part and be fixed in a known manner. After the desired length growth of the bone at a previously performed osteotomy has been completed, the distraction medullary mail can be removed again through the channel in the bone and be replaced by a solid shaft anchoring part of corresponding length, which thereafter remains part of the prosthesis. All of these measures can be performed via the side of the bone facing away from the joint replacement part without requiring repeated large operations in the region of the prosthesis, so that the risk of infection is minimized.

The locating means can be a radiation source being non-hazardous to patients, which is associated with the shaft anchoring part at its side facing away from the joint replacement part, wherein the channel can be formed in the required design through measuring for the radiation source from outside the bone section.

Advantageously, also a wire-shaped guide element protruding centrally from the attachment means can be used as the locating means, wherein the wire-shaped guide element passes through the bone section and protrudes therefrom to the outside. The connection between the guide element and the attachment means is advantageously designed to be releasable. This can be achieved, for example, by the fact that the attachment means has an internally threaded bore and the guide element has a corresponding external thread.

In order to facilitate withdrawal of the shaft anchoring part through the milled channel under tractive action of the tool, the shaft anchoring part is appropriately formed such that also a torque can be transmitted by the tool to the shaft anchoring part.

For this, the shaft anchoring part additionally includes a polygonal socket in front of the internally threaded bore towards the tool side. The tool used therein is designed to have two portions; Diametrically inside it has an element for traction force transmission, for example a tie rod having an external thread, and diametrically outside it has an element for transmission of the torque to the shaft anchoring part, for example a sleeve-shaped connection element having a polygonal plug.

In case a guide element is used as the locating means, the guide element is screwed out of the internally threaded bore forming the attachment means. Thereafter the tie rod can be led through the sleeve-shaped connection element and screwed into the internally threaded bore of the attachment means at the shaft anchoring part, in order to exert axial traction on the shaft anchoring part, while a torque can be transmitted from outside through polygonal engagement between the connection element and the attachment means, whereby the shaft anchoring means can be extracted by means of traction and torque.

Advantageously, a drill cutter is provided on the shaft anchoring part at the tool attachment side, which during rotation of the shaft anchoring part by means of the tool located outside the bone takes away any bone parts possibly protruding in the milled channel and thus facilitates withdrawal of the shaft anchoring part.

The surface of the shaft anchoring part is smooth, preferably polished and appropriately has a surface roughness depth of 0.1 µm or less. This largely excludes engagement of the living bone with the shaft anchoring part, so that the shaft anchoring part can be withdrawn from the medullary space without large resistance.

In order to enable withdrawal of the shaft anchoring part from the cavity of the shaft replacement part without any problems, the inner wall of the cavity is appropriately designed to be slide friction reducing, for example by applying a thin slide coating or by inserting a plastic sleeve.

Preferably, in the joint replacement part or the shaft replacement part there is provided a lateral bore opening into the cavity, wherein a cable can be led through said lateral bore, which cable can be connected at its one end to a subcutaneous antenna for supplying energy and at its other end to a drive of a distraction medullary nail when the latter is introduced into the shaft replacement part after the shaft anchoring part has been removed in order to perform bone distraction according to the callus distraction method.

During the first surgical operation, connection means can be mounted at the shaft replacement part in the region of its end facing away from the joint replacement part for fixing it to an adjoining bone section; however, said connection means do only gain in importance when a distraction is performed.

The shaft anchoring part over its length has an invariable diameter, but it may also taper towards the joint replacement part or have tapered sections, as may also be the case with a distraction medullary nail.

The shaft anchoring part can be a massive stabilizer or a medullary nail having an integrated drive for distraction.

In the configuration according to the invention, the implantable prosthesis with its joint forming part can be designed in a conventional manner, which has significant advantages, because the prosthesis lock to the tibia component can be designed in an essentially simpler and more stable manner, and the prosthesis does not have to be decoupled any more and can remain permanently in place. Also the connection to the shaft replacement part, the length of which can be designed to be variable and as short as possible, so that only the defect produced by the resection is bridged, can be designed conventionally, for example as a cone and screw connection.

In cases where a knee joint and the femur shaft portion near the knee joint are to be replaced, first the tibial joint component is implanted after a resection en bloc of the affected bone portion of the femur. In the case of children preferably a tibia plateau component with a PTFE inlay having a polished shaft anchoring part is used, wherein rotational stability is achieved via pins below the tibia plateau component. In the case of said arrangement the polished shaft anchoring part is able to slide under pressure of the growth cartilage obtained and the remaining growth potential of the proximal tibia growth cartilage can be utilized.

Subsequently, a guide wire is introduced into the greater trochanter in the frontal plane in extension of the medullary space and in the lateral plane at the height of the front one-third point of the proximal femur and is pushed forward through the medullary space from proximally up to the defect. The medullary space is milled out gradually via said guide wire as far as necessary for introducing the shaft anchoring part. Then the joint replacement part and the shaft replacement part are chosen depending on the size of the defect. Thereafter the straight shaft anchoring part adapted to the diameter of the medullary space and polished on the outside is introduced into the cavity of the shaft replacement part at the open side thereof and connected in a positive-locking manner by means of bolts or screws. Subsequently, the prosthesis can be placed in situ and be connected, on the one hand, to the guide wire in the central opening of the shaft anchoring part, which guide wire has previously been introduced from proximally, and, on the other hand, via the prosthesis lock to the tibia plateau component. The guide wire is cut off about one centimeter above the trochanter tip. Additionally an L-plate is mounted at the joint replacement part and the shaft replacement part, respectively, at their lateral side, wherein the later sliding segment is already at this time fixed via the L-plate by means of one or two small fragment screws.

For lengthening the remaining thigh bone, first the medullary space is milled out gradually corresponding to the diameter of the envisaged distraction medullary nail up to the height of the planned osteotomy by means of a straight cannulated milling tool adapted to the set guide wire. Subsequently, the bone is cut through in a minimally invasive manner, preferably by means of a medullary space saw. The milling operation is continued until the shaft anchoring part has been reached. Therein a possibly existing curvature of the bone can be overcome, because after osteotomy the two bone segments are normally very short and align towards one another. As soon as the shaft anchoring part has been reached, a cannulated extraction tool is introduced via the guide wire, wherein a polygonal plug at the end of the cannulated extraction tool engages in a corresponding polygonal socket in the shaft anchoring part, so that rotational forces for releasing the shaft anchoring part after removal of the positive-locking connection between the shaft anchoring part and the joint replacement part and the shaft replacement part, respectively, can be transmitted. Then the guide wire is screwed out of the attachment means and a tie rod is screwed through the cannulated tool into the thread of the attachment means. Therewith also an axial force can be exerted on the shaft anchoring part and the shaft anchoring part can be extracted towards the proximal direction. Herein a drill cutter at the side of the shaft anchoring part facing away from the joint replacement part can take off smaller intramedullary obstacles. Thereafter the distraction medullary nail is introduced into the cavity of the shaft replacement part through the bone channel formed in this way. The distraction medullary nail is connected in a positive-locking manner by means of bolts or screws, on the one hand, through the provided openings to the joint replacement part and the shaft replacement part, respectively, and on the other hand to the proximal femur. If an electromotive drive with a subcutaneous receiving antenna is used, it may be required depending on the embodiment that the drive is introduced in advance into the shaft replacement part. For this, the cable is introduced in advance through the channel in the proximal femur vai the osteotomy into the opening of the joint replacement part and the shaft replacement part with the aid of a strand or a wire and led out laterally.

A similar procedure is performed when replacing a hip joint and the femur shaft portion near to the hip joint. Unless hemiarthroplasty is envisaged, at first the hip socket is implanted after a resection en bloc of the affected bone portion. Subsequently a guide wire is intercondylarly introduced in the frontal plane centrally and in the lateral plane in extension of the distal femur shaft axis and advanced through the medullary space up into the defect. The medullary space is milled out gradually via said guide wire as far as necessary for introducing the shaft anchoring part. The joint replacement part and the shaft replacement part are chosen depending on the size of the defect. Then the straight shaft anchoring part adapted to the diameter of the medullary space and polished on the outside is introduced into the opening of the cavity of the shaft replacement part facing away from the joint replacement part and connected in a positive-locking manner by means of bolts or screws. Thereafter the prosthesis is placed in situ, wherein the guide wire is introduced into the central opening of the shaft anchoring part. The guide wire is cut off in the notch. Additionally an L-plate is mounted laterally at the joint replacement part and the shaft replacement part, respectively, wherein the later sliding segment is already at this time fixed via the L-plate by means of one or two small fragment screws.

After length grown has been completed, first the medullary space is milled out gradually corresponding to the diameter of the envisaged distraction medullary nail up to the height of the planned osteotomy by means of a straight cannulated milling tool adapted to the set guide wire. Subsequently, the bone is cut through in a minimally invasive manner, preferably by means of a medullary space saw. The milling operation is continued until the shaft anchoring part of the prosthesis has been reached. Therein a possibly existing curvature of the bone can be overcome, because after osteotomy the two bone segments are normally very short and align towards one another. As soon as the shaft anchoring part has been reached, a cannulated extraction tool is introduced via the guide wire, wherein a polygonal plug at the end of the cannulated extraction tool engages in a corresponding polygonal socket in the shaft anchoring part, so that rotational forces for releasing the shaft anchoring part after removal of the positive-locking connection between the shaft anchoring part and the joint replacement part and the shaft replacement part, respectively, can be transmitted. Then the guide wire is screwed out of the attachment means and a tie rod is screwed through the cannulated tool into the thread of the attachment means. Therewith also an axial force can be exerted on the shaft anchoring part and the shaft anchoring part can be extracted towards the distal direction. Herein a drill cutter at the side of the shaft anchoring part facing away from the joint replacement part can take off smaller intramedullary obstacles. Thereafter the distraction medullary nail is introduced into the cavity of the shaft replacement part through the bone channel formed in this way. The distraction medullary nail is connected in a positive-locking manner by means of bolts or screws, on the one hand, through the provided openings to the joint replacement part and the shaft replacement part, respectively, and on the other hand to the distal femur. If an electromotive drive with a subcutaneous receiving antenna is used, it may be required depending on the embodiment that the drive is introduced in advance into the shaft replacement part. For this, the cable is introduced in advance through the channel in the distal femur via the osteotomy into the opening of the joint replacement part and the shaft replacement part with the aid of a strand or a wire and led out laterally.

BRIEF DESCRIPTION OF THE DRAWINGS

Hereinafter an exemplary embodiment of the invention will be explained in greater detail by way of drawings, wherein.

DETAILED DESCRIPTION

Figure 1:
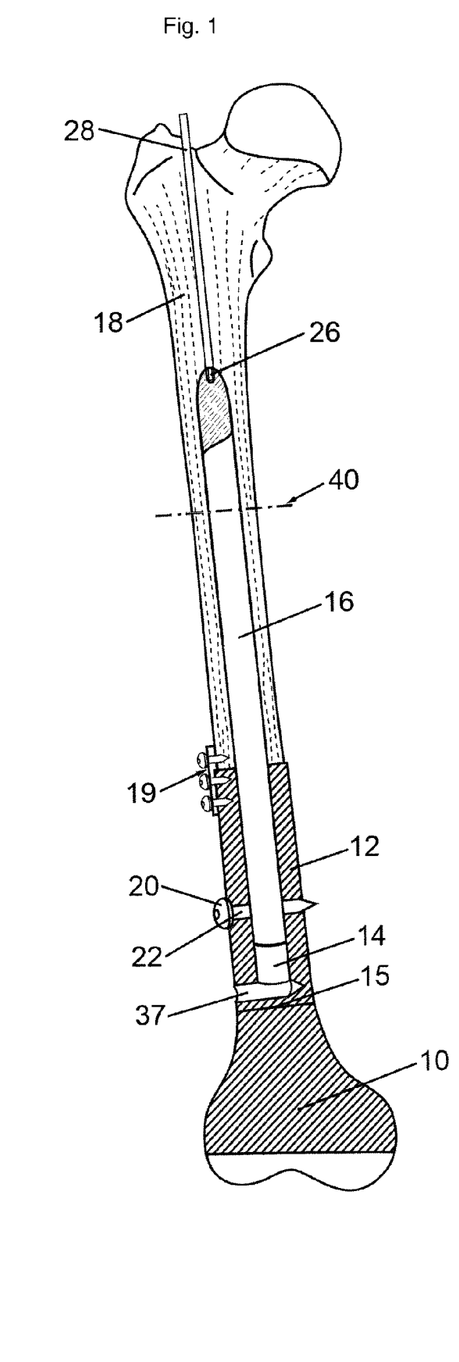
FIG. 1 shows a schematic view in longitudinal cross-section of an implantable prosthesis with adjoining bone section.

The implantable prosthesis shown in FIG. 1 comprises a joint replacement part 10, which is releasably connected to a shaft replacement part 12 for exchange purposes. The shaft replacement part 12 is connected to a bone section 18 through a plate 19 and screws.

A cavity 14 in the form of a central blind hole is formed in the shaft replacement part 12, which cavity 14 has a bottom 15 at the side of the joint replacement part 10 (in practice, the shaft replacement part 12 will surely be bored through, because appropriately the joint replacement part and the shaft replacement part are connected by a central screw) and is open at its side facing away from the joint replacement part 10. The inner wall of the cavity 14 is provided with a slide friction reducing coating. A shaft anchoring part 16 having a polished wall is inserted in the cavity 14. At the bottom 15 there is provided a lateral bore 37 in the shaft replacement part 12 for passing through a connection element, which can be connected with its one end to a drive of a distraction medullary nail 30 (FIGS. 4 to 11) inserted instead of the shaft anchoring part 16 and with its end located at the outside of the prosthesis to a subcutaneous receiver for supplying energy to the drive. The shaft anchoring part 16 is connected to the shaft replacement part 12 by means of a screw bolt 20 extending through a transverse bore 22 in the shaft replacement part 12 and in the shaft anchoring part 16.

At its end facing away from the joint replacement part 10, the shaft anchoring part 16 has attachment means 26 formed by an opening, which is releasably engaged, for example through a threaded joint, by locating means 28 in the form of a guide wire. The guide wire 28 extends from the shaft anchoring part 16, passes through the bone section 18 and exits it.

In the embodiment shown in FIG. 1 the guide wire 28 forms the guide for a milling tool located outside the bone section 18 for milling a channel 42 (FIG. 3) up to the free end of the shaft anchoring part 16, which then, after the screw bolt 20 has been released and pulled out, is removed through the milled channel 42 and can be replaced by a medullary nail 30 (FIGS. 4 to 11), which is correspondingly fixed by means of cross bolts 31 and 33, respectively (FIGS. 4 to 11), after an osteotomy of the bone has been performed along a partition plane 40 shown as a dash-dotted line by means of an inner saw (not shown).

Figure 2:
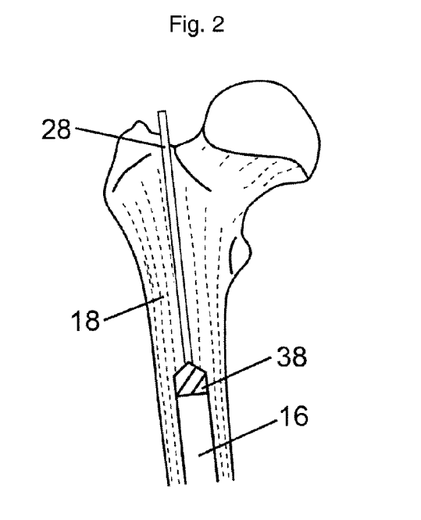
FIG. 2 shows a partial view in longitudinal cross-section of the bone section with an alternative embodiment of the portion of the shaft anchoring part of the prosthesis facing away from the joint replacement part.

In the embodiment shown in FIG. 2 a cutting drill 38 protrudes from the shaft anchoring part 16, which during rotation under traction of the shaft anchoring part 16 takes away potentially existing protrusions at the wall of the milled channel 42 (FIG. 3) and thus facilitates withdrawal of the shaft anchoring part 16 from the bone section 18 and subsequent insertion of a distraction medullary nail 30 (FIGS. 4 to 11).

Figure 3:
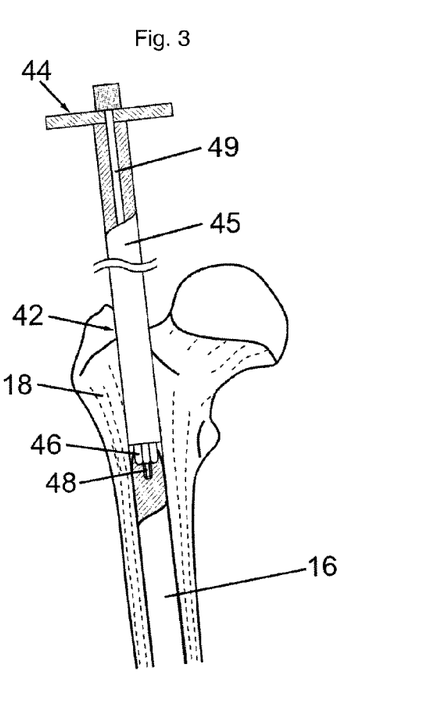
FIG. 3 shows a partial view in longitudinal cross-section of an extraction tool in engagement with the shaft anchoring part.

For withdrawing the shaft anchoring part 16 from the bone section 18 at its side facing away from the joint replacement part 10, the shaft anchoring part 16, as shown in FIG. 3, has a polygonal socket 46 at its end side and an adjoining internally threaded bore 48 for engagement with a sleeve-shaped connection element 45, which fits through the channel 42, of a tool 44 located outside the bone section 18. With a polygonal plug located at its end side, the connection element 45 engages in a positive-locking manner in the polygonal socket 46 of the shaft anchoring part 16. A tie rod 49 passing through the connection element 45 in a rotationally fixed manner is screwed with its end-sided external thread into the internally threaded bore 48 of the shaft replacement part 16. In this way the tool 44, when rotated, is able to transmit a traction force and a torque for easily extracting the shaft anchoring part 16.

FIGS. 4 to 11 describe variants of bone lengthening using a known distraction medullary nail 30 inserted instead of the extracted shaft anchoring part 16 (FIGS. 1 to 3).

Figure 4:
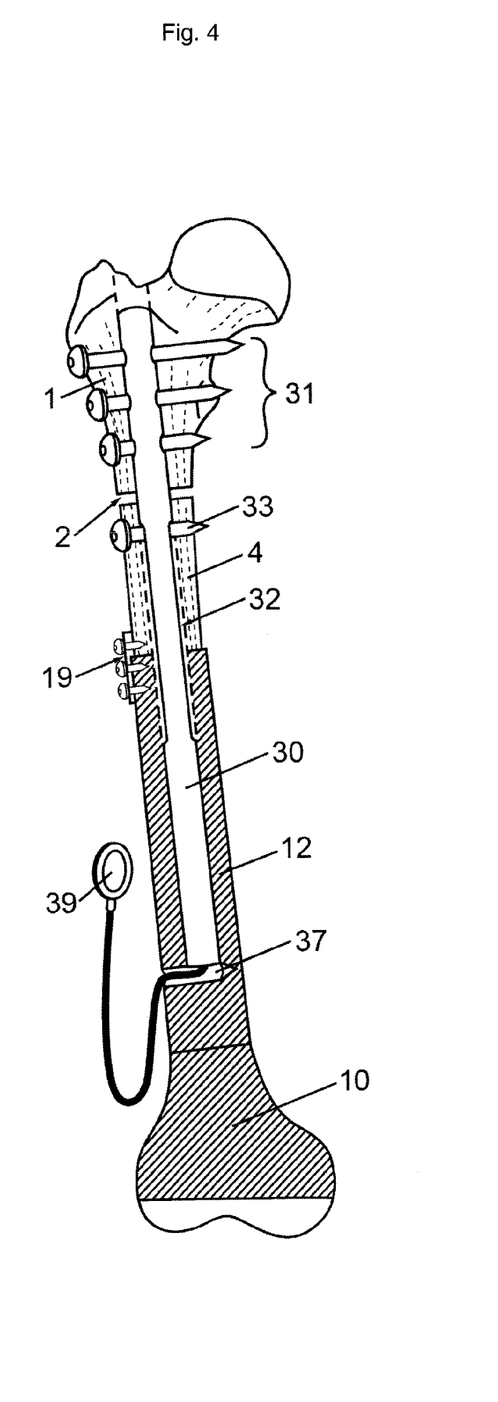
FIG. 4 shows a schematic view in longitudinal cross-section of a replacement of the distal femur by a first embodiment of a distraction medullary nail prior to distraction, the distraction medullary nail being inserted instead of the shaft anchoring part.
Figure 5:
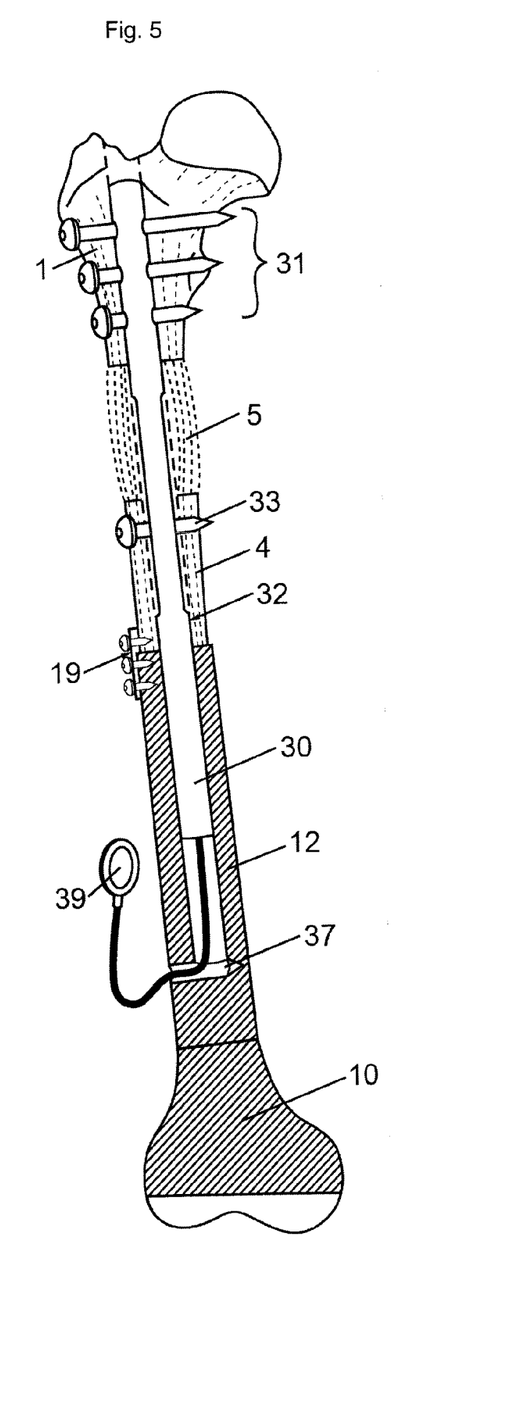
FIG. 5 in a view like in FIG. 3 shows the state after the distraction.

FIGS. 4 and 5 show a replacement of the distal femur bone, for example after resection of a bone tumor. A joint replacement part 10 and a shaft replacement part 12 are shown. A distraction medullary nail 30 having an elongated hole 32 is introduced from proximally in a positive-locking, but axially slidable manner into the shaft replacement part 12. The distraction medullary nail 30 is fixed, for example, by means of one or, more advantageously, three screws 31, as shown, in the proximal femur bone 1 (in FIGS. 1 to 3 bone section 18), whereby also very proximal osteotomies 2 (in FIGS. 1 to 3 partition plane 40) become possible. A fixation distally of the osteotomy 2 is done in the proximal end of the elongated hole 32 also by means of a screw 33. An axial distraction force can be exerted on the bone via said screw 33 by means of a drive in the medullary nail 30, for example by means of a gear motor, and thus the bone can be lengthened according to the callus distraction method in the osteotomy gap 2 by formation of callus 5. The physiological antecurvation of the femur does not constitute a hindrance for inserting a straight medullary nail 30, because the femur is straightened at the osteotomy 2. An electric cable for connecting an inside drive to an antenna 39 located in the subcutaneous fatty tissue is led out through the lateral bore 37, wherein energy can be coupled in from the outside via the antenna 39.

Figure 6:
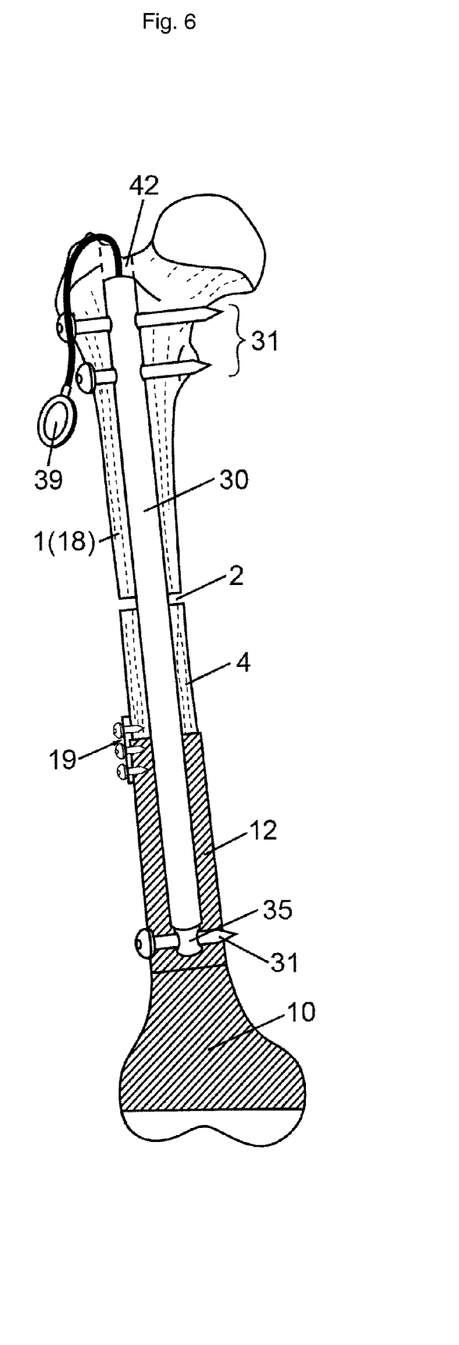
FIG. 6 in a view like in FIG. 3 shows a replacement of the distal femur by a second embodiment of a distraction medullary nail prior to distraction, the distraction medullary nail being inserted instead of the shaft anchoring part.
Figure 7:
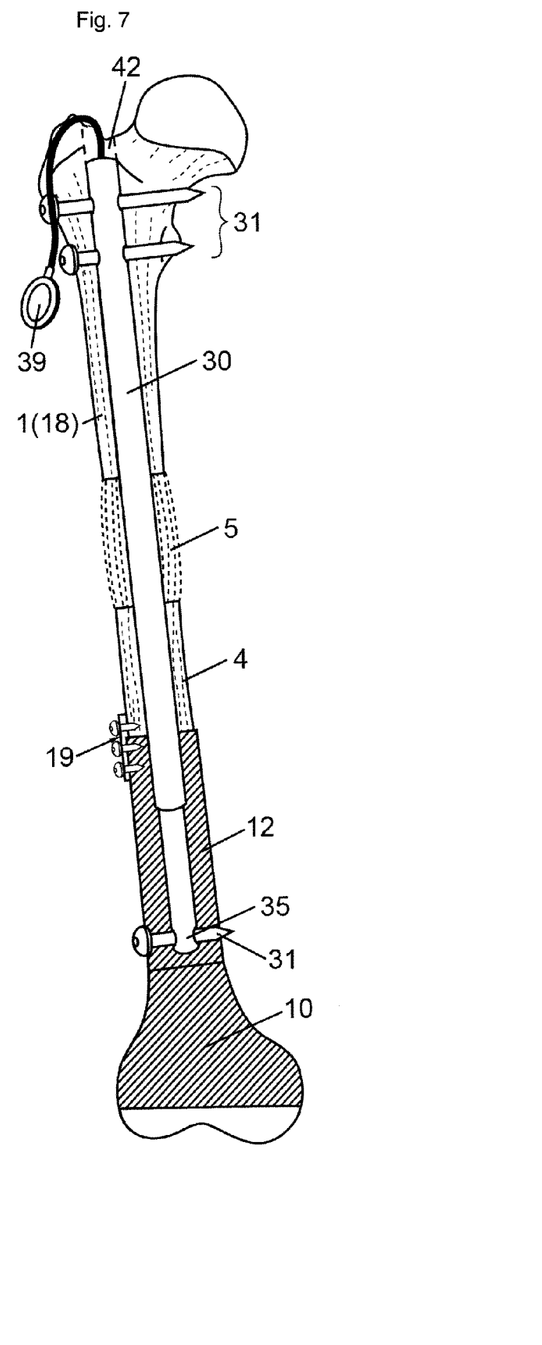
FIG. 7 in a view like in FIG. 5 shows the state after the distraction.

FIGS. 6 and 7 essentially correspond to FIGS. 4 and 5. Here lengthening is done by means of a distraction medullary nail 30 having a telescopic mechanism 35, wherein the distraction medullary nail 30 is, on the one hand, anchored by means of screws 31 in the proximal femur bone 1 (in FIGS. 1 to 3 bone section 18) and, on the other hand, fixed in a positive-locking manner by means of a further screw 31 in the shaft replacement part 12. In order to increase strength in the middle of the shaft, i.e. the point of maximal bending stress, the telescopic medullary nail 30 can be sunk into the shaft replacement part 12 far enough for it to remain, even at its extended state, still sufficiently far with the large diameter in the shaft replacement part 12. In this configuration the cable for the antenna 39 is led out through the milled-out channel 42.

Figure 8:
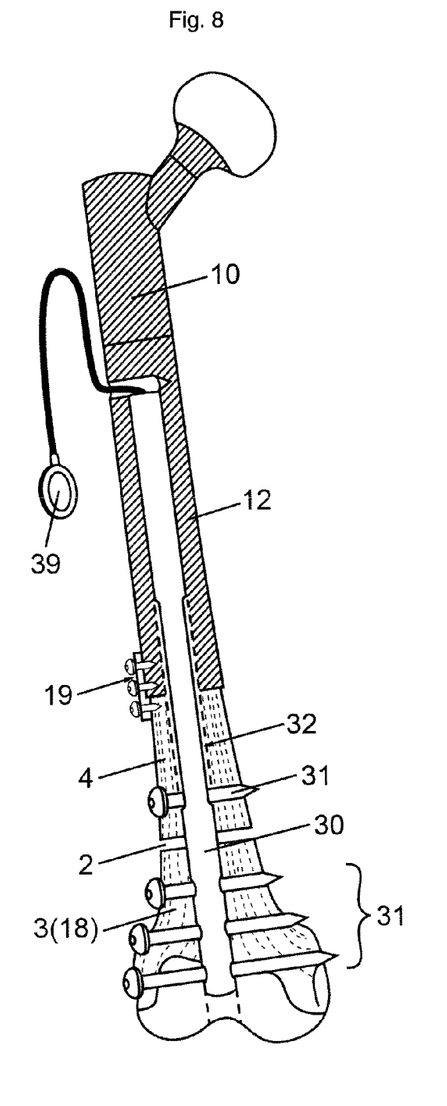
FIG. 8 in a view like in FIG. 3 schematically shows a replacement of the proximal femur by a first embodiment of the distraction medullary nail prior to distraction.
Figure 9:
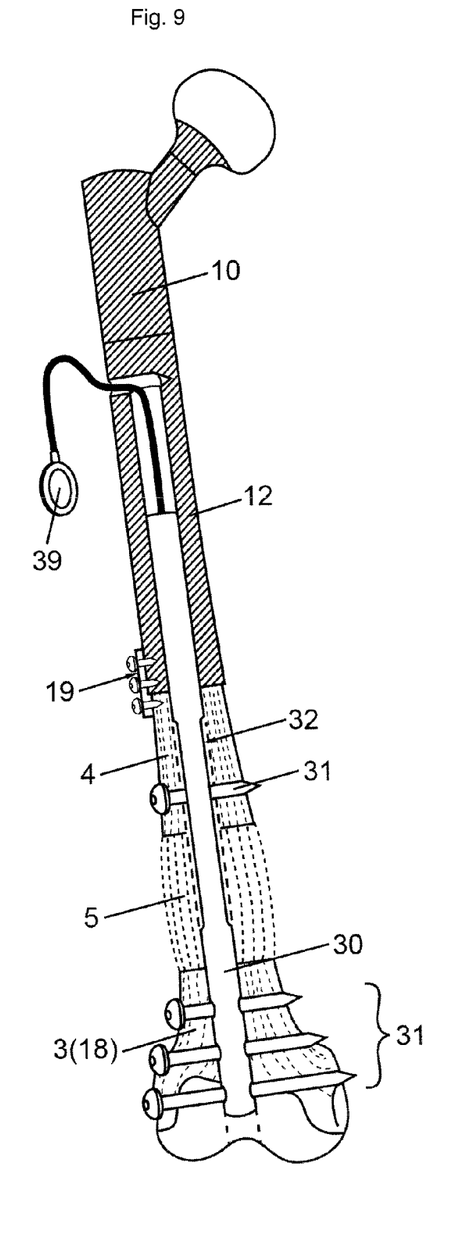
FIG. 9 in a view like in FIG. 7 shows the state after the distraction.

FIGS. 8 and 9 show a replacement of the proximal femur bone, for example after resection of a bone tumor. A distraction medullary nail 30 having an elongated hole 32 is introduced from distally from the knee joint through the distal femur bone in an axially slidable manner into the shaft replacement part 12, wherein the distraction medullary nail 30 is anchored, on the one hand, by means of several screws 31 in the distal femur 3 (functionally corresponding to the bone section 18 of FIGS. 1 to 3) and, on the other hand, by means of a further screw 31 in the distal elongated hole and the remaining femur shaft 4, which is connected to the shaft replacement part 12 through connection means 19 in the form of an L-shaped plate. An axial distraction force can be exerted on the bone via the elongated hole 32 in the medullary nail by means of a drive, for example by means of a gear motor, within the medullary nail 30 and thus the bone can be lengthened according to the callus distraction method (callus 5) in the osteotomy gap 2 (partition plane 40 of FIGS. 1 to 3).

Figure 10:
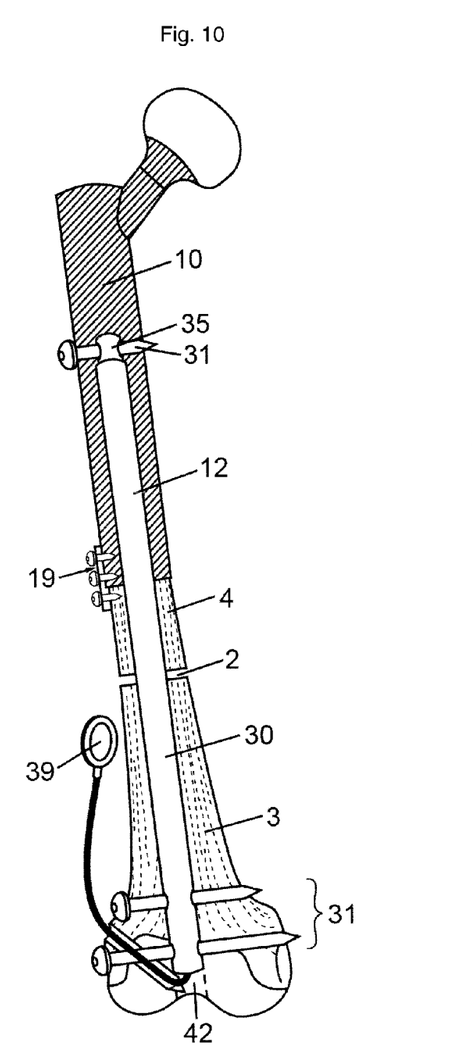
FIG. 10 in a view like in FIG. 7 schematically shows a replacement of the proximal femur by a second embodiment of the distraction medullary nail prior to distraction.
Figure 11:
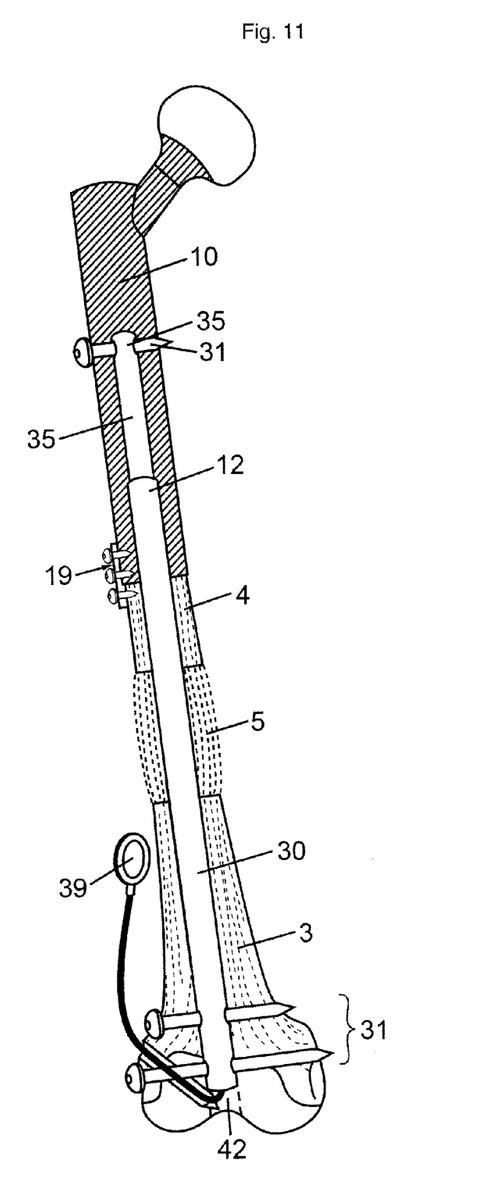
FIG. 11 in a view like in FIG. 9 shows the state after the distraction.

FIGS. 10 and 11 essentially correspond to FIGS. 8 and 9. Here, however, lengthening (callus 5) is done by means of a distraction medullary nail 30 having a telescopic mechanism 35 analogously to FIGS. 6 and 7, wherein the distraction medullary nail 30 is fixed by means of screws 31 in the distal femur 3 and by means of a further screw 31 in the shaft replacement part 12. In order to increase strength in the middle of the shaft, i.e. the point of maximal bending stress, the telescopic medullary nail 30 can here also be sunk into the shaft replacement part far enough for it to remain, even at its extended state, still sufficiently far with the large diameter in the shaft replacement part 12. In this configuration the cable for the antenna 39 is led out through the milled-out channel 42.

The invention claimed is:

1. An implantable prosthesis system for replacing a human hip or knee joint and the adjoining bone sections, comprising:
    a joint replacement part (10);
    a shaft replacement part (12) being connectable to the joint replacement part (10) or integral therewith and having a central cavity (14); and
    a rod-shaped shaft anchoring part (16) being insertable into the cavity (14) in the shaft replacement part (12);
    wherein the rod-shaped shaft anchoring part (16) comprises a proximal and distal part, wherein the proximal part being insertable into the cavity in the shaft replacement part and the distal part comprises a locating means (28) adapted to form a channel (42) through a patient's bone section (18) located at a side facing away from the joint replacement part from outside, the channel (42) and the rod-shaped shaft anchoring part (16) are aligned along a common axis and wherein the channel (42) extends up to the distal part of the rod-shaped shaft anchoring part (16); and
    attachment means (26) for engagement with a tool (44) projecting from outside the bone section (18) through the channel (42) for exerting at least a traction force on the rod-shaped shaft anchoring part (16) for removing the rod-shaped shaft anchoring part (16) from the bone section (18) through the channel (42).

2. The implantable prosthesis system according to claim 1, wherein the locating means (28) is a radiation source.

3. The implantable prosthesis system according to claim 2, wherein the guide element (28) can be releasably connected to the attachment means (26).

4. The implantable prosthesis system according to claim 1, wherein the locating means (28) is a wire-shaped guide element protruding centrally from the attachment means (26), wherein the wire-shaped guide element passes through the bone section (18) and protrudes therefrom to the outside.

5. The implantable prosthesis system according to claim 1, wherein the shaft anchoring part (16) is formed such that a torque can be transmitted by the tool (44) to the rod-shaped shaft anchoring part (16).

6. The implantable prosthesis system according to claim 1, wherein the attachment means (26) has an internally threaded bore (48).

7. The implantable prosthesis system according to claim 6, wherein a polygonal socket (46) is provided in the rod-shaped shaft anchoring part (16) in front of the internally threaded bore (48) towards the tool.

8. The implantable prosthesis system according to claim 1, wherein the rod-shaped shaft anchoring part (16) has a drill cutter (38) at the tool attachment side.

9. The implantable prosthesis system according to claim 1, wherein a surface of the rod-shaped shaft anchoring part (16) has a surface roughness depth of 0.1 μm or less.

10. The implantable prosthesis system according to claim 1, wherein an inner wall of the cavity (14) in the shaft replacement part (12) is designed to be slide friction reducing.

11. The implantable prosthesis system according to claim 1, wherein the shaft replacement part (12), at an end facing away from the joint replacement part, has a lateral bore (37) opening into the cavity (14).

12. The implantable prosthesis system according to claim 11, wherein a connection means (19) for fixing it to an adjoining bone section can be mounted at the shaft replacement part (12) in a region of the end facing away from the joint replacement part.

13. The implantable prosthesis system according to claim 1, wherein the rod-shaped shaft anchoring part (16) over its length has an invariable diameter and/or a diameter tapered towards the joint replacement part (10).

14. The implantable prosthesis system according to claim 1, wherein the rod-shaped shaft anchoring part (16) comprises a stabilizer or a medullary nail.

\* \* \* \* \*